United States Patent
Shinada et al.

(10) Patent No.: US 9,366,656 B2
(45) Date of Patent: Jun. 14, 2016

(54) ANALYSIS DEVICE PROVIDED WITH DISCHARGE IONIZATION CURRENT DETECTOR

(71) Applicant: SHIMADZU CORPORATION, Kyoto-shi, Kyoto (JP)

(72) Inventors: Kei Shinada, Kyoto (JP); Shigeyoshi Horiike, Kyoto (JP); Takahiro Nishimoto, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 38 days.

(21) Appl. No.: 14/384,049

(22) PCT Filed: Feb. 20, 2013

(86) PCT No.: PCT/JP2013/054079
§ 371 (c)(1),
(2) Date: Sep. 9, 2014

(87) PCT Pub. No.: WO2013/140920
PCT Pub. Date: Sep. 26, 2013

(65) Prior Publication Data
US 2015/0042354 A1    Feb. 12, 2015

(30) Foreign Application Priority Data
Mar. 21, 2012   (JP) .................................. 2012-064172

(51) Int. Cl.
| | |
|---|---|
| *G01N 27/62* | (2006.01) |
| *G01N 30/64* | (2006.01) |
| *G01N 27/70* | (2006.01) |
| *G01N 30/88* | (2006.01) |

(52) U.S. Cl.
CPC ............... *G01N 30/64* (2013.01); *G01N 27/70* (2013.01); *G01N 2030/645* (2013.01); *G01N 2030/8813* (2013.01)

(58) Field of Classification Search
CPC ....... G01N 27/62; G01N 27/70; G01N 27/60; G01N 27/68; G01N 30/64; G01N 21/67; G01N 21/69; G01N 21/82
See application file for complete search history.

(56) References Cited

U.S. PATENT DOCUMENTS

| | | | | |
|---|---|---|---|---|
| 5,394,092 A | * | 2/1995 | Wentworth | ............ G01N 27/70 324/455 |
| 5,892,364 A | * | 4/1999 | Monagle | ................ G01N 27/70 324/459 |
| 2011/0187379 A1 | | 8/2011 | Shinada et al. | |

FOREIGN PATENT DOCUMENTS

| | | |
|---|---|---|
| JP | 9-96609 A | 4/1997 |
| JP | 2011-158357 A | 8/2011 |

OTHER PUBLICATIONS

Gras et al., "Gas Chromatographic Applications with the Dielectric Barrier Discharge Detector", Journal of Chromatographic Science, vol. 44, Feb. 2006, 9 pages.

(Continued)

*Primary Examiner* — Minh N Tang
(74) *Attorney, Agent, or Firm* — Westerman, Hattori, Daniels & Adrian, LLP

(57) ABSTRACT

An analysis device comprising a discharge ionization current detector, a plasma gas supply section, a sample gas supply section, a flow rate setting condition holding section and a gas flow rate setting means controller. The flow rate setting condition holding section holds, as a flow rate setting condition, a relationship between a sample gas supply flow rate from the sample gas supply section and a supply flow rate of plasma gas to be set with respect to the sample gas supply flow rate and the gas flow rate controller is configured to set a plasma gas supply flow rate from the plasma gas supply section to a flow rate according to the sample gas supply flow rate, based on the flow rate setting condition held in the flow rate setting condition holding section.

8 Claims, 5 Drawing Sheets

(56) References Cited

OTHER PUBLICATIONS

Tang et al., Characterization and mechanism studies of dielectric barrier discharges generated at atmospheric pressure, Applied Physics Letters, vol. 96, 191503, 2010, 3 pages.

Verner, "Photoionization Detection and Its Application in Gas Chromatography" Journal of Chromatography, vol. 300, 1984, pp. 249-264.

International Search Report dated May 21, 2013 issued in corresponding application No. PCT/JP2013/054079.

* cited by examiner

ANALYSIS DEVICE PROVIDED WITH DISCHARGE IONIZATION CURRENT DETECTOR

TECHNICAL FIELD

The present invention relates to an analysis device provided with a discharge ionization current detector, and more particularly, to an analysis device provided with a discharge ionization current detector adopting a method for generating dielectric-barrier discharge at a plasma generation section and ionizing a sample by light that is emitted at the time of generation of dielectric-barrier discharge.

BACKGROUND ART

As a trace gas detector for a gas chromatograph, detectors adopting various methods, such as a TCD (Thermal Conductive Detector) and an ECD(Electric Capture Detector), are being proposed and put to practical use, and a detector that is currently most generally used is an FID (Flame Ionization Detector). The FID achieves a wide dynamic range (about six figures) by ionizing sample gas by a hydrogen flame and measuring the ionization current.

Furthermore, a detector which generates an excited species of inert gas, such as He, $N_2$, Ar, Ne or Xe, by plasma that is generated by high-voltage discharge, and which thereby ionizes a sample is proposed. For example, a PDD (Pulsed Discharge Detector) generates plasma by causing spark discharge by application of a pulsed high voltage. A method that uses plasma does not need hydrogen and generally, the ionization efficiency thereof is higher than that of the FID. For example, the ionization efficiency for propane is 0.0005% for the FID and 0.07% for the PDD.

With respect to generation of plasma by a method different from that of the PDD, there is a method that uses dielectric-barrier discharge (see Non-Patent Document 1). With the dielectric-barrier discharge, since the surface of an electrode for generating discharge is covered with a dielectric material, there is not much emission of thermal electrons, secondary electrons and the like that occur in the case of generating discharge by using metal electrodes, and the stability of plasma generation is high. Further, a discharge current is suppressed by the dielectric material, and thus, there are characteristics that deterioration of electrodes and heat generation at electrodes may be suppressed, and that the durability is high.

As the PDD or an ionization detector that uses dielectric-barrier discharge, there is one that performs ionization of a sample by mixing, in the sample, an excited species generated by plasma generated by discharge, and a discharge ionization current detector that performs ionization of a sample by excitation light that is emitted at the time of generation of plasma by discharge (see Patent Document 1, Non-Patent Document 2).

PRIOR ART DOCUMENTS

Patent Documents

Patent Document 1: Japanese Patent Laid-open Publication No. 2011-158357

Non-Patent Documents

Non-Patent Document 1: "Gas Chromatographic Applications with the Dielectric Barrier Discharge Detector", Journal of Chromatographic Science, Vol. 44, February 2006

Non-Patent Document 2: "PHOTOIONIZATION DETECTION AND ITS APPLICATION IN GAS CHROMATOGRAPHY", Journal of Chromatography, 300(1984) p 249-264

Non-Patent Document 3: "Characterization and mechanism studies of dielectric barrier discharge generated at atmospheric pressure", APPLIED PHYSICS LETTERS 96,

SUMMARY OF THE INVENTION

Problems to be Solved by the Invention

A discharge ionization current detector is generally provided with a sample ionization section, which is a space for ionizing a sample, provided on the downstream side of a tube through which plasma gas for generating plasma is to flow, and a sample is to be injected into the sample ionization section by a capillary from the opposite direction of a plasma generation section. If sample gas enters the plasma generation section, generation of discharge is affected and the discharge state in the plasma generation section becomes unstable, and thus, the flow rate of plasma gas has to be at a certain level or higher so that sample gas does not enter the plasma generation section.

Also, with the discharge method of the PDD or the like, plasma gas also serves the role of cooling a discharge electrode, and since the discharge state changes depending on the cooling state of the discharge electrode, plasma gas is desirably made to flow at a constant flow rate by which the effect of cooling the discharge electrode may be sufficiently achieved. With a conventional discharge ionization current detector, detection was performed with the flow rate of plasma gas fixed at a sufficiently high level based on the circumstances described above. Accordingly, a great amount of plasma gas was consumed at all times.

Furthermore, at the sample ionization section, sample gas and plasma gas are mixed, and the sample gas is diluted by the plasma gas. Conventionally, the plasma gas had to be made to flow at a high flow rate, and the concentration of the sample gas at a detection section where an ionized sample was to be detected was reduced, and it was difficult to achieve a high detection sensitivity.

Accordingly, the present invention has its aim to provide an analysis device provided with a discharge ionization current detector that is capable of suppressing the consumption amount of plasma gas and of achieving a high detection sensitivity.

Solutions to the Problems

The present invention is an analysis device provided with a discharge ionization current detector including a plasma generation section that generates dielectric-barrier discharge by applying high AC voltage between a plurality of electrodes attached on an outer circumference of a dielectric tube, a sample ionization section that is arranged on a side of one end of the dielectric tube and that ionizes a sample by excitation light emitted at a time of discharge in the plasma generation section, and a sample ion detection section that detects a sample ionized by the sample ionization section as a current. This analysis device is provided with a plasma gas supply section for supplying plasma gas from a side of the other end of the dielectric tube while variably adjusting a flow rate of the plasma gas; a sample gas supply section for supplying sample gas to the sample ionization section from a side opposite the dielectric tube; a flow rate setting condition holding section for holding, as a flow rate setting condition, a relationship between a sample gas supply flow rate from the sample gas supply section and a supply flow rate of plasma gas to be set with respect to the supply flow rate; and gas flow rate setting means configured to set a plasma gas supply flow rate from the plasma gas supply section to a flow rate according to the sample gas supply flow rate, based on the flow rate setting condition held in the flow rate setting condition holding section.

Effects of the Invention

The present invention has been made on the basis of the knowledge that, with a discharge ionization current detector adopting a method of ionizing a sample by generating excitation light by dielectric-barrier discharge, heat generation by discharge electrodes is small, and cooling of the electrodes by plasma gas is almost not necessary. That is, the flow rate of plasma gas may be such that sample gas is merely prevented from getting mixed in plasma gas. With the analysis device of the present invention, a plasma gas supply section for supplying plasma gas to a dielectric tube of a discharge ionization current detector is capable of variably adjusting a supply flow rate of the plasma gas. Additionally, there are provided a flow rate setting condition holding section for holding, as a flow rate setting condition, a relationship between a sample gas supply flow rate from a sample gas supply section and a supply flow rate of plasma gas to be set with respect to the supply flow rate, and gas flow rate setting means configured to set a plasma gas supply flow rate from the plasma gas supply section to a flow rate according to the sample gas supply flow rate on the basis of the flow rate setting condition held in the flow rate setting condition holding section, and thus, the supply flow rate of plasma gas can be set to a minimum flow rate that is in accordance with the supply flow rate of sample gas. Accordingly, the consumption amount of plasma gas can be suppressed, and also, the dilution rate of sample gas may be reduced and the detection sensitivity may be increased.

EMBODIMENTS OF THE INVENTION

Figure 1:
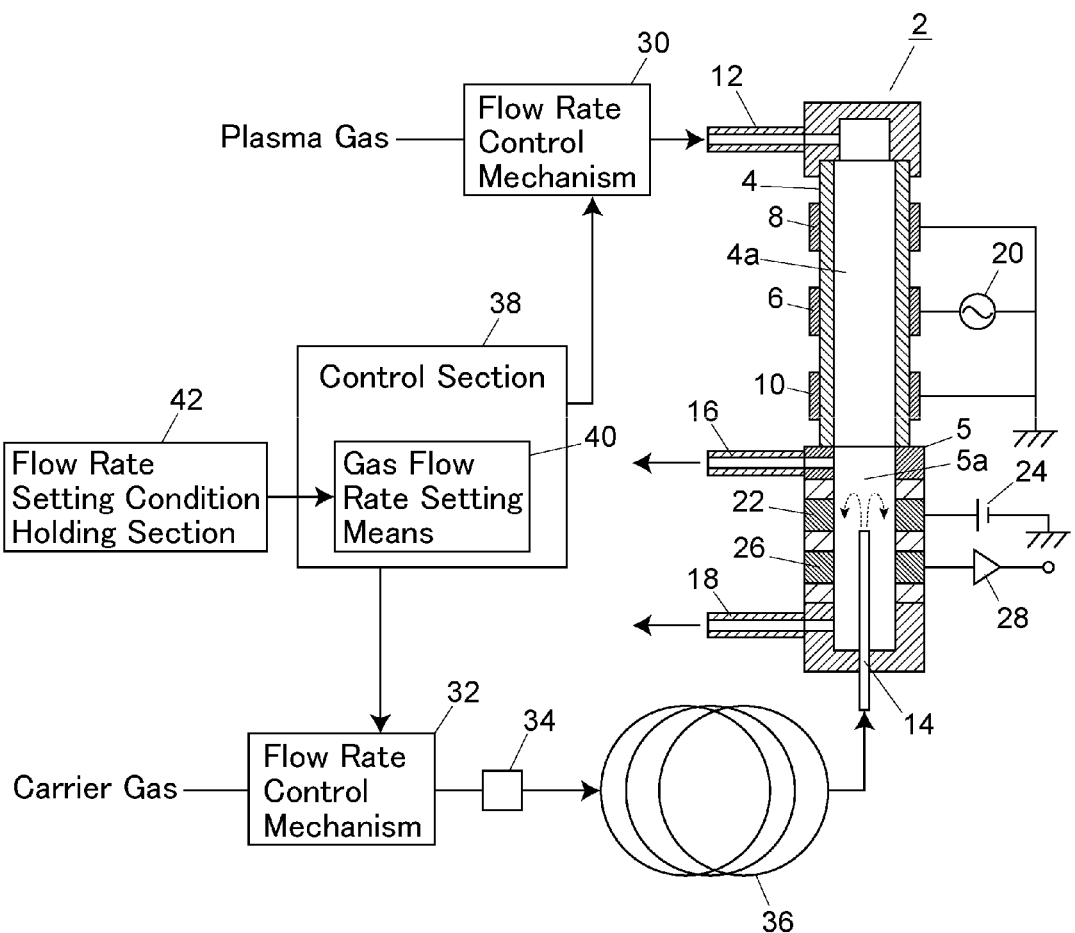
FIG. 1 is a cross-sectional view of a schematic configuration showing an embodiment of an analysis device provided with a discharge ionization current detector.

According to an analysis device of the present invention, flow rate setting conditions held in a flow rate setting condition holding section desirably include, as a minimum setting condition, a relationship between a sample gas supply flow rate and a minimum plasma gas supply flow rate that does not allow sample gas to enter a plasma generation section, as contrasted with the sample gas supply flow rate, and gas flow rate setting means is desirably configured to set the plasma gas supply flow rate from a plasma gas supply section by using the minimum setting condition, when a detection sensitivity of a discharge ionization current detector is set at the highest sensitivity. The analysis device may then be provided with a function of performing detection with the highest sensitivity while suppressing the consumption amount of plasma gas at the minimum.

As the minimum setting condition mentioned above, a relational expression expressing a correlation of the plasma gas supply flow rate to the sample gas supply flow rate based on coefficients determined in advance according to the type of sample gas and the temperature of the discharge ionization current detector may be cited.

The following equation may be cited as an example of the relational expression mentioned above.

$$Vp = f(Vc) \times K1 \times K2$$

It is to be noted that $Vp$ is a plasma gas flow rate, $Vc$ is a carrier gas flow velocity, $f(Vc)$ is a function of the carrier gas flow velocity $Vc$, $K1$ is a coefficient according to the type of sample gas, and $K2$ is a coefficient according to the temperature of the discharge ionization current detector.

The analysis device according to the present invention may be applied to a gas chromatograph for carrying a sample to an analytical column by carrier gas, separating the sample into components at the analytical column, and introducing the separated component into a discharge ionization current detector. Generally, with the gas chromatograph, a sample includes a solvent, and the concentration of the solvent is the highest among components to be introduced into the discharge ionization current detector. In this case, if conditions regarding the flow rate of carrier gas, and the type and the temperature of the analytical column are the same, the time slot when the solvent appears as a peak in a chromatogram is constant at all times, and thus, a time slot when the solvent will be introduced into the discharge ionization current detector may be predicted. Accordingly, with the analysis device of the present invention, the gas flow rate setting means is desirably configured to set the plasma gas supply flow rate in a time slot when a component other than the solvent is to be introduced into the discharge ionization current detector to be lower than the plasma gas supply flow rate in a time slot when the solvent is to be introduced into the discharge ionization current detector. Then, since the plasma gas supply flow rate in a time slot when the solvent with the highest concentration in sample gas is being introduced into the discharge ionization current detector may be set to a flow rate which does not allow the solvent to enter the plasma generation section, and the plasma gas supply flow rate in a time slot when components other than the solvent are being introduced into the discharge ionization current detector may be set to a flow rate lower than the flow rate mentioned above, components other than the solvent may be measured with a high sensitivity.

In the following, an embodiment of a gas chromatograph which is an analysis device provided with a discharge ionization current detector will be described with reference to the drawings. FIG. 1 is a cross-sectional view of a schematic configuration showing an embodiment of the gas chromatograph.

A discharge ionization current detector 2 is provided as a detector for detecting a sample component separated by the gas chromatograph. The discharge ionization current detector 2 is provided with a plasma generation section, a sample ionization section and a sample ion detection section.

The plasma generation section is configured by a dielectric tube 4 formed of quartz, for example, and ring electrodes 6, 8 and 10 attached at three positions separate from one another on the outer circumference of the dielectric tube 4. High AC voltage is to be applied to the electrode 6 by an AC power supply 20. The two electrodes 8 and 10 arranged on the opposite sides of the electrode 6 are grounded. A gas inlet 12 is provided at one end of the dielectric tube 4, and helium is supplied to a passage 4a inside the dielectric tube 4 from the gas inlet 12 as plasma gas. When high AC voltage is applied to the electrode 6, dielectric-barrier discharge occurs between the electrode 6 and the electrode 8 and between the electrode 6 and the electrode 10, and plasma gas flowing through the passage 4a in the dielectric tube 4 is excited by the discharge, thereby emitting excitation light.

It is to be noted that, as the plasma gas, one of argon, nitrogen, neon and xenon, or mixed gas thereof may also be used instead of helium.

One end of a tube 5 forming the sample ionization section and the sample ion detection section is connected on the side of the other end, which is the downstream side, of the dielectric tube 4. A capillary 14 is inserted in the other end of the tube 5. The capillary 14 is for supplying sample gas from an analytical column 36 of the gas chromatograph into a space 5a inside the tube 5, and is arranged facing the other end of the dielectric tube 4. Sample gas is injected from a tip end of the capillary 14 toward the dielectric tube 4.

The tube 5 includes, from the side of the one end connected to the downstream end of the dielectric tube 4, a bias electrode 22 and a charge collecting electrode 26. The bias electrode 22 and the charge collecting electrode 26 are both ring electrodes. DC voltage is to be applied to the bias electrode 22 by a DC power supply 24. The tip end of the capillary 14 is present between a connection portion of the tube 5 and the dielectric tube 4, and the charge collecting electrode 26, and components in sample gas injected from the tip end of the capillary 14 are ionized by excitation light that is emitted at the time of generation of dielectric-barrier discharge in the plasma generation section and are charged. Potential is applied to the ionized sample by the bias electrode 22, and then, the charge is collected by the charge collecting electrode 26 and is outputted as a current signal after being amplified by a current amplifier 28.

A gas outlet 16 is provided on a side wall on the side of the one end of the tube 5, and a gas outlet 18 is also provided on a side wall on the side of the other end of the tube 5. The gas outlet 16 is provided on the side more to the one end than the bias electrode 22, and the gas outlet 18 is provided on the side more to the other end than the charge collecting electrode 26. A part of plasma gas from the dielectric tube 4 is discharged from the gas outlet 16, and the rest of the plasma gas from the dielectric tube 4 and sample gas pushed back by the plasma gas are discharged from the gas outlet 18.

The flow rate of plasma gas to be supplied to the plasma generation section is adjusted by a flow rate control mechanism 30 such as a flow controller. The flow rate of sample gas to be injected from the tip end of the capillary 14 is determined by the carrier gas flow rate that is adjusted by a flow rate control mechanism 32 such as a flow controller. The passage from the flow rate control mechanism 23 is connected to a sample introduction section 34, and the sample introduction section 34 is connected to the analytical column 36, and the analytical column 36 is connected to the capillary 14.

The flow rate control mechanisms 30 and 32 are controlled by a control section 38. The control section 38 is provided with gas flow rate setting means 40 for controlling the flow rate control mechanisms 30 and 32. The control section 38 may be realized by a computer for controlling the gas chromatograph, or a general-purpose computer such as a personal computer connected to the gas chromatograph. The gas flow rate setting means 40 may be realized by a program stored in a storage device of a computer configuring the control section 38. A flow rate setting condition holding section 42 is shown as a separate body from the control section 38, but may be realized by the storage device of the computer configuring the control section 38, or it may alternatively be realized by a storage device separate from the computer configuring the control section 38.

The gas flow rate setting means 40 is configured to set the plasma gas flow rate according to the carrier gas flow rate determined based on a measurement sample. The carrier gas flow rate is set by an analyst according to the type of sample which is the measurement target, and the object of the analysis. The analyst sets the carrier gas flow rate according to demands such as to perform an analysis in a state where the separation performance for the sample is high, to shorten the measurement time, or to suppress the consumption amount of carrier gas.

The gas flow rate setting means 40 is configured to determine, as the minimum flow rate, based on the carrier gas flow rate set in the above manner, the minimum plasma gas flow rate by which sample gas does not reach the plasma generation section configured by the dielectric tube 4 and the electrodes 6, 8 and 10, and to set a flow rate at or above the minimum flow rate as the plasma gas flow rate in response to a demand from the analyst.

The minimum flow rate is determined based on a flow rate setting condition held in the flow rate setting condition holding section 42. By setting the minimum flow rate as the plasma gas flow rate, the consumption amount of plasma gas may be suppressed to the minimum, and also, the detection sensitivity for a sample may be increased by reducing the dilution rate of sample gas. The gas flow rate setting means 40 sets the minimum flow rate as the plasma gas flow rate in the case where the analyst demands to perform measurement with the highest sensitivity. Additionally, the analyst may also freely set the plasma gas flow rate at or above the minimum flow rate through the gas flow rate setting means 40.

The plasma generation section of this discharge ionization current detector 2 is for generating dielectric-barrier discharge, and thus, there is almost no heat generation at the electrodes 6, 8 and 10, and the cooling effect on the electrodes 6, 8 and 10 by plasma gas does not have to be taken into consideration. Accordingly, it is enough if the flow rate of plasma gas is such that sample gas injected from the tip end of the capillary 14 does not reach the plasma generation section configured by the dielectric tube 4 and the electrodes 6, 8 and 10.

Whether sample gas reaches the plasma generation section or not depends on whether the component gas can be diffused against the plasma gas flow or not, and is determined based on the ratio of the flow rates of carrier gas and plasma gas, and also, on the type of sample gas (a component with the highest concentration) and the temperature. The flow rate setting condition holding section 42 holds, as one of the flow rate setting conditions, the following equation (1), which is the condition (the minimum setting condition) for determining the minimum flow rate by which sample gas does not reach the plasma generation section.

$$Vp = f(Vc) \times K1 \times K2 \quad (1)$$

Here, Vp is the plasma gas flow rate, Vc is the carrier gas flow velocity, f(Vc) is the function for the carrier gas flow velocity (for example, Vc×0.3), K1 is a coefficient according to the type of sample gas, and K2 is a coefficient according to the temperature. The flow rate setting condition holding section 42 holds, in addition to the equation (1), f(Vc), K1 and K2 which have actually been measured according to the device configuration. Additionally, the type of sample gas is a component with the highest concentration among the sample gas components separated by the gas chromatograph, and generally, the solvent is the component with the highest concentration.

Figure 2:
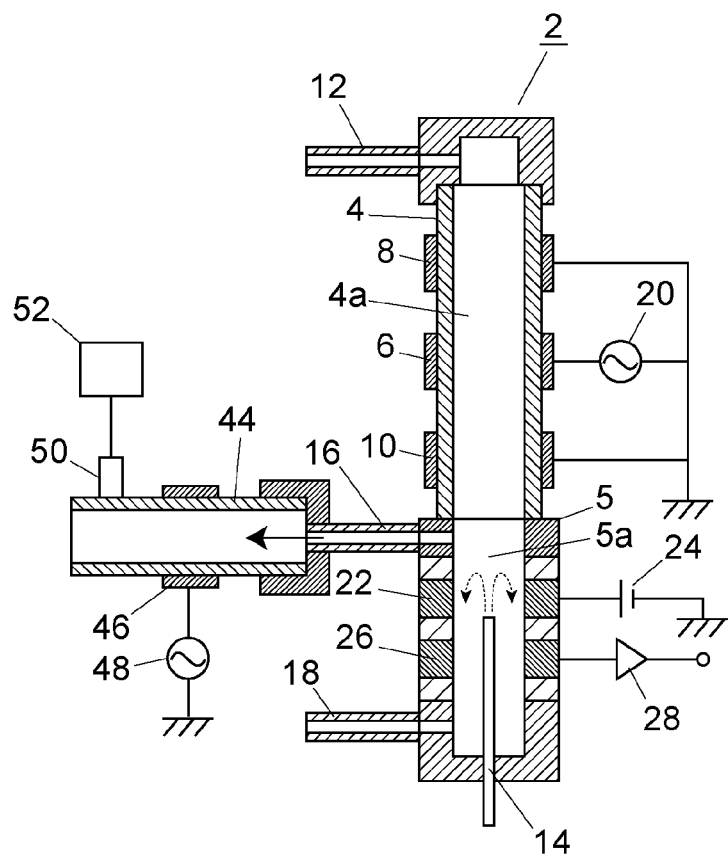
FIG. 2 is a cross-sectional view of a schematic configuration showing an example of a device configuration at the time of setting a setting condition for plasma gas flow rate according to the embodiment.

An example of the way of determining each coefficient in the equation (1), which is the minimum setting condition, will be described. As shown in FIG. 2, a dielectric tube 44 is connected to the gas outlet 16 of the discharge ionization current detector 2 of the analysis device in FIG. 1, and discharge is generated inside the dielectric tube 44 by attaching a ring electrode 46 on the outer circumference of the dielectric tube 44 and applying high AC voltage by an AC power supply 48. Plasma light emission inside the dielectric tube 44 is captured by an optical fiber 50, and is detected by a spectroscopic detector (optical detector) 52.

Figure 3:
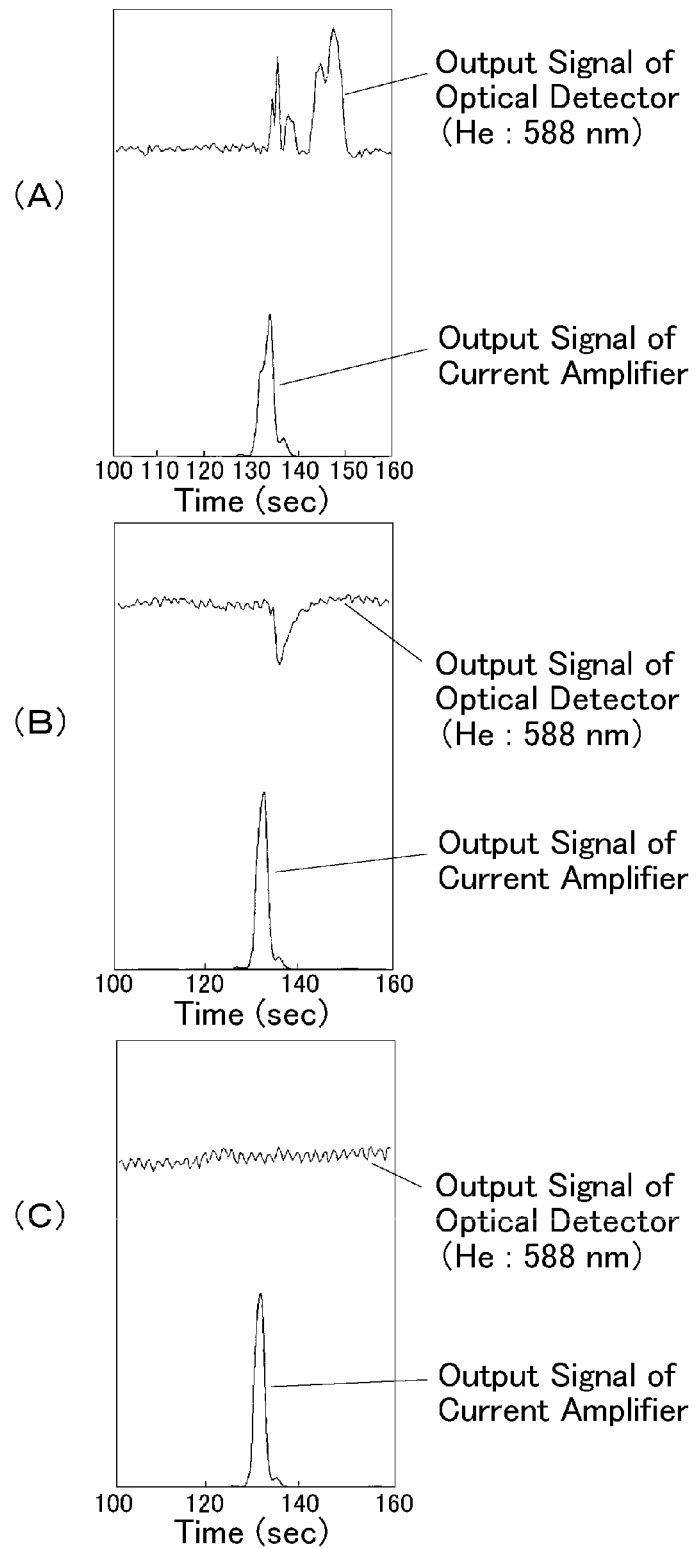
FIGS. 3(A) to 3(C) are waveform graphs of a detection signal of an optical detector and an output signal of a current amplifier of the device configuration in FIG. 2, and (A) shows a case where the flow velocity of plasma gas is set at 5 cm per second, (B) shows a case where the flow velocity of plasma gas is set at 7.5 cm per second, and (C) shows a case where the flow velocity of plasma gas is set at 10 cm per second.

FIGS. 3(A) to 3(C) are output signals of the optical detector 52 and of the current amplifier 28 acquired by the configuration in FIG. 2. In this measurement, n-hexane is used as the sample, the detector temperature is made constant at a reference temperature (200° C.), the carrier gas flow rate is fixed at 50 ccm (flow velocity: 30 cm per second), and the plasma gas flow velocity is set to (A) 5 cm per second, (B) 7.5 cm per second, and (C) 10 cm per second, and the spectrum of light with a wavelength of 588 nm is measured by the optical detector 52. In the data of (A) and (B), peaks appear in the output signals of the optical detector 52. This indicates that the sample is discharged from the gas outlet 16. On the other hand, in the data of (C), no peak appear in the output signal of the optical detector 52, and it can be seen that the sample is not discharged from the gas outlet 16. Accordingly, with this device configuration and measurement conditions, n-hexane, which is the sample, does not enter the passage 4a in the dielectric tube 4 if the plasma gas flow velocity is set to 10 cm per second (carrier gas flow velocity: 30 cm per second×0.3) or more.

Accordingly, with the device configuration and the measurement conditions as the standard conditions, f(Vc) is set to 0.3 Vc, the coefficient K1 regarding the solvent used in this measurement is set to 1, and the coefficient K2 regarding the temperature at the time of this measurement to 1, and these are stored in the flow rate setting condition holding section 42. By taking the plasma gas flow velocity at this time (10 cm per second) as the standard, and determining, according to the same apparatus configuration, the plasma gas flow velocity by which the sample is not discharged from the gas outlet 16 by performing measurement in the same manner by using another solvent that may be used by the gas chromatograph as a sample component, the coefficient K1 regarding the solvent in the equation (1) may be determined from the ratio between the plasma gas flow velocity which is the standard and the plasma gas flow rate which has been determined. In the same manner, by performing measurement by changing the detector temperature and determining the plasma gas flow velocity by which the sample is not discharged from the gas outlet 16, the coefficient K2 regarding the detector temperature in the equation (1) may be determined from the ratio between the plasma gas flow velocity which is the standard and the plasma gas flow velocity which has been determined.

Figure 4:
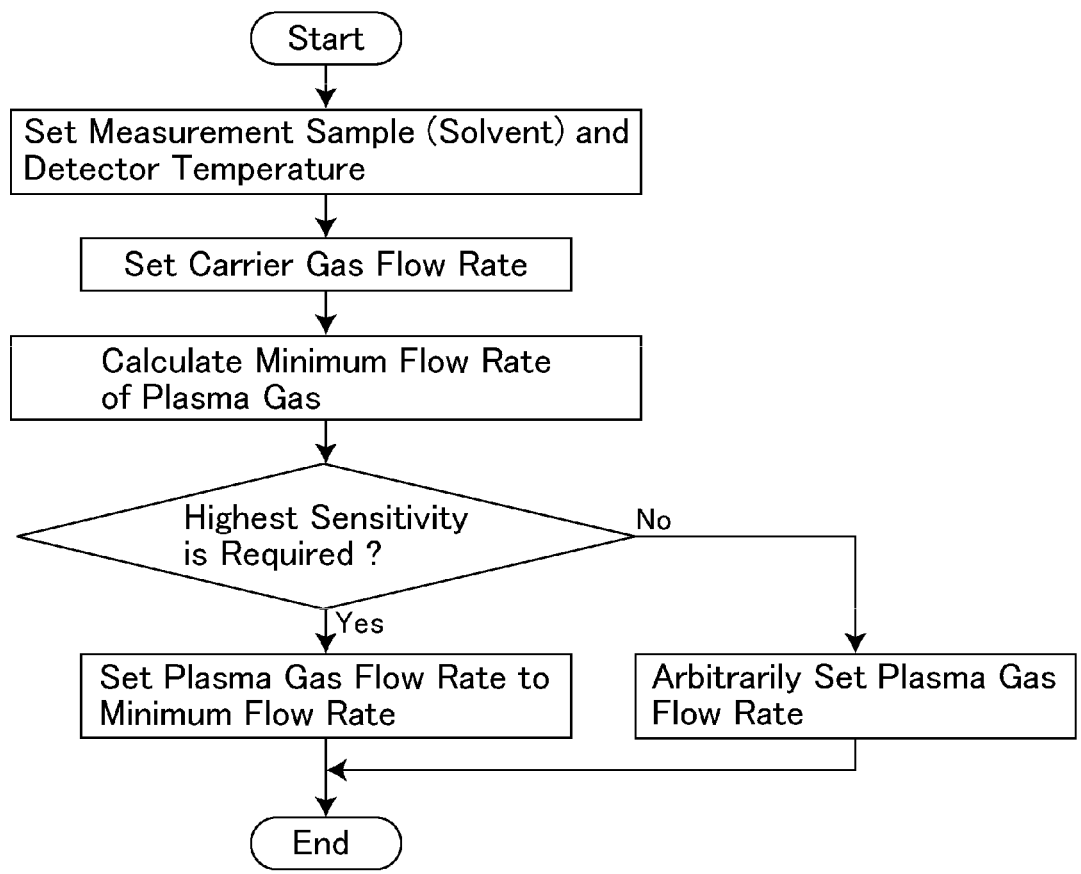
FIG. 4 is a flow chart showing a procedure for setting a plasma gas flow rate.

A procedure for setting the plasma gas flow rate will be described with reference to FIG. 4.

An analyst sets, in the device, the type of component with the highest concentration in sample gas (normally, a solvent), the detector temperature, and the carrier gas flow rate in accordance with the object of the analysis. The gas flow rate setting means 40 of the control section 38 determines the minimum flow rate of the plasma gas flow rate based on the pieces of information inputted by the analyst and the minimum setting condition held in the flow rate setting condition holding section 42, and in the case where measurement with the highest sensitivity is required by the analyst, the minimum flow rate is set as the plasma gas flow rate. In the case where measurement with the highest sensitivity is not required by the analyst, the gas flow rate setting means 40 makes the analyst set an arbitrary flow rate which is at or above the minimum flow rate as the plasma gas flow rate.

Also, generally, a sample to be introduced into the analytical column 36 is a sample component which is an analysis target mixed in a solvent. In this case, of the sample components separated by the analytical column 36, the component with the highest concentration is the solvent. Since the composition and the concentration of the solvent are known, the time slot of introduction into the discharge ionization current detector 2 through the analytical column 36 is the same at all times and may be predicted, if the carrier gas flow rate, and the type and the temperature of the analytical column 36 are the same.

Figure 5:
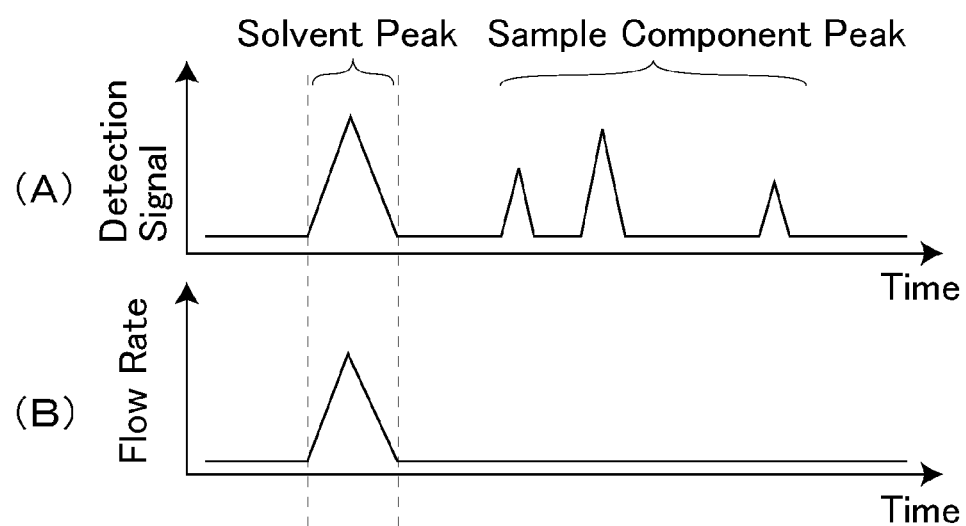
FIGS. 5(A) and 5(B) are diagrams for describing a method of controlling the plasma gas flow rate according to a sample component, and (A) is a chromatogram that is obtained by a discharge ionization detector, and (B) is a graph showing a change over time of the plasma gas flow rate.

Accordingly, the gas flow rate setting means 40 may be configured to be able to set the plasma gas flow rate for each time slot. Since the peak in a chromatogram does not have to be measured with a high sensitivity for the solvent, the plasma gas flow rate may be set to a high flow rate by which the solvent does not reach the plasma generation section only in a time slot when the solvent, which is a component with a high concentration, is being introduced into the discharge ionization current detector 2, and in other time slots, the plasma gas flow rate may be set to a low flow rate by which components other than the solvent do not reach the plasma generation section, as shown in FIGS. 5(A) and 5(B). The consumption amount of plasma gas may thereby be reduced, and sample components other than the solvent may be detected with a high sensitivity while pollution of the plasma generation section by the solvent is reliably prevented. In this case, the minimum flow rate determined for the solvent by the equation (1) described above may be set as the plasma gas flow rate for the time slot when the solvent is being introduced into the discharge ionization current detector 2, and the minimum flow rate determined for a component with the highest concentration among the sample components besides the solvent by the equation (1) may be set as the plasma gas flow rate for other time slots. Additionally, if the sample components other than the solvent are unknown, a predetermined flow rate (for example, half the minimum flow rate for the solvent) may be set.

DESCRIPTION OF REFERENCE SIGNS

2: Discharge ionization current detector
4: Dielectric tube
6, 8, 10: Discharge electrode
12: Plasma gas inlet
14: Capillary (for introducing sample gas)
16, 18: Gas outlet
20: High-voltage AC power supply
22: Bias electrode
24: DC power supply 26: Charge collecting electrode
28: Current amplifier
30, 32: Flow rate control mechanism
34: Sample introduction section
36: Analytical column
38: Control section
40: Gas flow rate control means
42: Flow rate setting condition holding section

What is claimed is:

1. An analysis device comprising:
a discharge ionization current detector including a plasma generation section that generates dielectric-barrier discharge by applying high AC voltage between a plurality of electrodes attached on an outer circumference of a dielectric tube, a sample ionization section that is arranged on a side of one end of the dielectric tube and that ionizes a sample by excitation light emitted at a time of discharge in the plasma generation section, and a sample ion detection section that detects a sample ionized by the sample ionization section as a current;
a plasma gas supply section for supplying plasma gas from a side of the other end of the dielectric tube while variably adjusting a flow rate of the plasma gas;
a sample gas supply section for supplying sample gas to the sample ionization section from a side opposite the dielectric tube;
a flow rate setting condition holding section for holding, as a flow rate setting condition, a relationship between a sample gas supply flow rate from the sample gas supply section and a supply flow rate of plasma gas to be set with respect to the sample gas supply flow rate; and
a gas flow rate controller configured to set a plasma gas supply flow rate from the plasma gas supply section to a flow rate according to the sample gas supply flow rate, based on the flow rate setting condition held in the flow rate setting condition holding section,
wherein the flow rate setting condition held in the flow rate setting condition holding section includes, as a minimum setting condition, a relationship between the sample gas supply flow rate and a minimum plasma gas supply flow rate that does not allow sample gas to enter the plasma generation section, as contrasted with the sample gas supply flow rate.

2. The analysis device according to claim 1,
wherein the gas flow rate controller is configured to set the plasma gas supply flow rate from the plasma gas supply section by using the minimum setting condition when a detection sensitivity of the discharge ionization current detector is set to a highest sensitivity.

3. The analysis device according to claim 2, wherein the minimum setting condition is a relational expression expressing a correlation of the plasma gas supply flow rate to the sample gas supply flow rate based on coefficients determined in advance according to a type of sample gas and a temperature of the discharge ionization current detector.

4. The analysis device according to claim 3, wherein the relational expression is expressed by the following equation:

$$Vp = f(Vc) \times K1 \times K2$$

where $Vp$ is a plasma gas flow rate, $Vc$ is a carrier gas flow velocity, $f(Vc)$ is a function of the carrier gas flow velocity $Vc$, $K1$ is a coefficient according to the type of sample gas, and $K2$ is a coefficient according to the temperature of the discharge ionization current detector.

5. The analysis device according to claim 4,
wherein the analysis device is a gas chromatograph for carrying a sample to an analytical column by carrier gas, separating the sample into components at the analytical column, and introducing a separated component into the discharge ionization current detector,
wherein the sample includes a solvent, and the solvent is a component with a highest concentration among components to be introduced into the discharge ionization current detector, and
wherein the gas flow rate controller is configured to set a plasma gas supply flow rate in a time slot when a component other than the solvent is to be introduced into the discharge ionization current detector to be lower than a plasma gas supply flow rate in a time slot when the solvent is to be introduced into the discharge ionization current detector.

6. The analysis device according to claim 3,
wherein the analysis device is a gas chromatograph for carrying a sample to an analytical column by carrier gas, separating the sample into components at the analytical column, and introducing a separated component into the discharge ionization current detector,
wherein the sample includes a solvent, and the solvent is a component with a highest concentration among components to be introduced into the discharge ionization current detector, and
wherein the gas flow rate controller is configured to set a plasma gas supply flow rate in a time slot when a component other than the solvent is to be introduced into the discharge ionization current detector to be lower than a plasma gas supply flow rate in a time slot when the solvent is to be introduced into the discharge ionization current detector.

7. The analysis device according to claim 2,
wherein the analysis device is a gas chromatograph for carrying a sample to an analytical column by carrier gas, separating the sample into components at the analytical column, and introducing a separated component into the discharge ionization current detector,
wherein the sample includes a solvent, and the solvent is a component with a highest concentration among components to be introduced into the discharge ionization current detector, and
wherein the gas flow rate controller is configured to set a plasma gas supply flow rate in a time slot when a component other than the solvent is to be introduced into the discharge ionization current detector to be lower than a plasma gas supply flow rate in a time slot when the solvent is to be introduced into the discharge ionization current detector.

8. The analysis device according to claim 1,
wherein the analysis device is a gas chromatograph for carrying a sample to an analytical column by carrier gas, separating the sample into components at the analytical column, and introducing a separated component into the discharge ionization current detector,
wherein the sample includes a solvent, and the solvent is a component with a highest concentration among components to be introduced into the discharge ionization current detector, and
wherein the gas flow rate controller is configured to set a plasma gas supply flow rate in a time slot when a component other than the solvent is to be introduced into the discharge ionization current detector to be lower than a plasma gas supply flow rate in a time slot when the solvent is to be introduced into the discharge ionization current detector.

* * * * *